United States Patent
Xie et al.

(10) Patent No.: US 7,087,373 B2
(45) Date of Patent: Aug. 8, 2006

(54) METHODS FOR DETERMINING PLASMA FREE DRUG CONCENTRATION BY DIRECT MEASUREMENT OF BINDING AFFINITY OF PROTEASE INHIBITORS TO PLASMA PROTEINS

(75) Inventors: Dong Xie, Germantown, MD (US); Wei Cao, Centereach, NY (US); John W. Erickson, Frederick, MD (US)

(73) Assignee: Tibotec Pharmaceuticals Ltd., County Cork (IE)

( * ) Notice: Subject to any disclaimer, the term of this patent is extended or adjusted under 35 U.S.C. 154(b) by 0 days.

(21) Appl. No.: 10/161,613

(22) Filed: Jun. 5, 2002

(65) Prior Publication Data

US 2003/0113748 A1    Jun. 19, 2003

Related U.S. Application Data

(60) Provisional application No. 60/295,557, filed on Jun. 5, 2001.

(51) Int. Cl.
*C12Q 1/37* (2006.01)
*G01N 33/53* (2006.01)
*G01N 33/48* (2006.01)

(52) U.S. Cl. ............................. 435/4; 435/7.1; 435/23; 702/19

(58) Field of Classification Search ................ 424/9.1, 424/9.2; 435/4, 5, 6, 7.1, 23; 514/12, 26, 514/29; 530/350, 362, 363; 702/19
See application file for complete search history.

(56) References Cited

U.S. PATENT DOCUMENTS

| | | | |
|---|---|---|---|
| 5,750,493 A | 5/1998 | Sommadossi et al. | |
| 5,783,398 A * | 7/1998 | Marcy et al. | 435/7.1 |
| 6,242,190 B1 * | 6/2001 | Freire et al. | 435/6 |
| 2002/0193318 A1* | 12/2002 | Burke et al. | 514/26 |

OTHER PUBLICATIONS

Acosta et al., Clinical Infectious Disease, vol. 30 Supp. 2, pp. S151-S159 (Jun. 2000).*
Sadler et al., Antimicrobial Agents and Chemotherapy, vol. 45 No. 3, pp. 852-856 (Mar. 2001).*
Bilello et al., Journal of Infectious Disease, vol. 171, pp. 546-551 (1991).*
Acosta E P, "Pharmacokinetic enhancement of protease inhibitors", Journal of Acquired Immune Deficiency Syndromes. Feb. 1, 2002; 29 Suppl 1:S11-8.
Du Souich et al., "Plasma protein binding and pharmacological response." Clin Pharmacokinet., 1993 24(6):435-40.
Zhang et al., "The Effect of Increasing alpha 1-Acid Glycoprotein Concentration on the Antiviral Efficacy of Human Immunodeficiency Virus Protease Inhibitors". J. Infect. Dis. (1999) 180:1833-1837.
Lindup, W. E. "Methods for the measurement of drug binding to plasma proteins." Methods Clin. Pharmacol., Proc. Int. Symp. (1980), Meeting Date 1979, 267-73. Publisher: Vieweg, Wiesbaden, Fed. Rep. Germany.
Hilgeroth A. et al. "Plasma protein binding properties of dimeric 4-aryl-1,4-dihydropyridines as novel non peptidic HIV-1 protease inhibitors." Pharmazie (2000), 55(7), 542-543.
Bilello J A et al. "Relevance of plasma protein binding to antiviral activity and clinical efficacy of inhibitors of human immunodeficiency virus protease." Journal of Infectious Diseases (Jun. 1996), 173(6), 1524-6.
Campoy A et al. "The use of isothermal titration calorimetry in drug design: Applications to high affinity binding and protonation/deprotonation coupling." Netsu Sokutei (2001), 28(2), 68-73.
Xie D et al. "Thermodynamics and proton uptake for pepstatin binding to retroviral and eukaryotic aspartic proteases," Advances in Experimental Medicine and Biology (1998), 436(Aspartic Proteinases), 381-386.
Leavitt S et al. "Direct measurement of protein binding energetics by isothermal titration calorimetry." Current Opinion in Structural Biology (Oct. 2001), 11(5), 560-6.
Chen X et al."The Binding Database: data management and interface design." Bioinformatics (2002), 18(1), 130-139.
Lopez M et al. "Isothermal titration calorimetry." Methods in Molecular Biology (2002), 173(Calcium-Binding Protein Protocols, vol. 2), 121-126.
Chen X et al."BindingDB: A Web-accessible molecular recognition database." Combinatorial Chemistry and High Throughput Screening (2001), 4(8), 719-725.
Pierce M et al. "Isothermal Titration Calorimetry of Protein-Protein Interactions." Methods (Orlando, Florida) (1999), 19(2), 213-221.

* cited by examiner

*Primary Examiner*—James C. Housel
*Assistant Examiner*—Zachariah Lucas
(74) *Attorney, Agent, or Firm*—Woodcock Washburn LLP

(57) ABSTRACT

Methods for isothermal titration calorimetry analysis of the binding affinity of protease inhibitors to plasma proteins. A method that can quantitatively calculate free drug concentrations of protease inhibitors in human plasma, as well as a method to calculate therapeutic amounts and dosage regimens. Furthermore, the present invention provides a method that can calculate the effect of plasma proteins on the antiviral activity (EC50 values) of protease inhibitors from their binding affinities to plasma proteins. The present invention provides as well a method that can evaluate the in vivo anti-HIV efficacy of PIs in human plasma.

3 Claims, 5 Drawing Sheets

METHODS FOR DETERMINING PLASMA FREE DRUG CONCENTRATION BY DIRECT MEASUREMENT OF BINDING AFFINITY OF PROTEASE INHIBITORS TO PLASMA PROTEINS

CROSS-REFERENCE TO RELATED APPLICATIONS

This application claims the benefit of priority under 35 U.S.C. § 119(e) to U.S. Provisional Application No. 60/295,557, filed on Jun. 5, 2001.

FIELD OF THE INVENTION

The present invention relates to methods for isothermal titration calorimetry analysis of the binding affinity of protease inhibitors to plasma proteins.

BACKGROUND OF THE INVENTION

Following administration, drugs are transported in biological fluids (e.g. in blood) partly in solution as free drug and partly bound to blood components (e.g., plasma proteins, blood cells). The physiologically active substances are in equilibrium between a free form and a form bound to endogenous ligands present in the same fluids (see reviews by Kremer, et al. Pharmacol Rev. 1988, 40:1–47). Only free drug is available for passive diffusion to target tissue sites where the desired biological activity may take place. When compared to the total-substance level, the free drug concentration is more closely related to drug concentration at the active site, to drug effects, and to clinical effectiveness. Observations made on both healthy and pathologically afflicted humans confirmed that the patients' clinical condition correlates better with variations in free form concentration when compared to variations in total substance concentrations.

Slight changes in the binding affinity of drugs to blood components can result in significant changes in clinical response or can even cause a toxic response. Since it is the free drug in plasma which equilibrates with the pharmacologically active site, a slight change in the binding affinity, such as from 99 to 98% binding, can result in an almost 100% change in free drug concentration, and, thus, can cause a significant alteration in response. This is the case for most HIV protease inhibitors (PIs) (Acosta, Acquir Immune Defic Syndr. 2002 Feb. 1; 29 Suppl 1:S11–8; Sadler, et al. Antimicrob Agents Chemother. 2001 March; 45(3):852–6; Anderson, et al, AIDS. 2000 Oct. 20;14(15):2293–7; Bilello, et al., J Infect Dis. 1995 March;171(3):546–51).

The binding of drugs to plasma proteins may influence their distribution, elimination and pharmacological effect, which is considered more closely related to unbound rather than total drug concentration (du Souich et al, 1993, Clin Pharmacokinet. 24:435–40.). Human serum albumin (HSA) and human α1-acid glycoprotein (AAG) are two mainly involved proteins in the binding of HIV PIs in plasma. Human AAG is an acute-phase protein whose expression increases during acute inflammatory episodes, infections, injuries, neoplastic disease, and AIDS (Kremer et al, Pharmacol Rev. 1988, 40: 1–47; Oie et al, 1993, J Acquir Immune Defic Syndr Hum Retrovirol. 5:531–533; Mackiewicz et al, 1995, Glycoconj. J. 12:241–247; van Dijk et al, 1995, Glycoconj J. 12:227–233). The level of AAG in human serum fluctuates between 0.15 and 1.5 mg/mL, and the average value may vary by as much as 4-fold between healthy volunteers and AIDS patients (Kremer et al, Pharmacol Rev. 1988, 40: 1–47; Oie et al, 1993, J Acquir Immune Defic Syndr Hum Retrovirol. 5:531–533). Additionally, AAG concentrations have been suggested to vary by race or ethnicity (Johnson et al, 1997, J. Pharm. Sci. 86: 1328–1333). It has been reported that AAG exists as a mixture of two or three genetic variants (the A variant and the F1 and/or S variants) in the plasma of most individuals (Hervé et al, 1998, Mol. Pharmacol. 54:129–138), which present different drug binding specificities.

The question whether AAG binding had an effect on in vivo antiviral activity of anti-HIV PIs has recently heightened the great interest in the investigations of effects of serum proteins on activity and pharmacokinetics of anti-HIV PIs in vitro (Billello et al. 1995, J. Infect. Dis. 171:546–551; Bilello et al. 1996, Antimicrobiol. Agents Chemother. 40:1491–1497; Lazdins et al. 1996, J. Infect. Dis. 175: 1063–1070; Kiriyama et al. 1996, Biopharmac. Drug Dispos. 17:739–751; Zhang et al. 1999, J. Infect. Dis. 180: 1833–1837; Jones et al. 2001, Br J Clin Pharmacol. 51:99–102; Kageyama et al. 1994, Antimicrob Agents Chemother. 22:499–506; Livingstone et al. 1995, J. Infect Dis. 172:1238–45), and in vivo (Sadler et al. 2001, Antimicrob. Agents Chemother. 45:852–856.). In vitro these studies have consistently demonstrated that human AAG reduced the antiviral activity of most PIs by decreasing the amount of free drug available for interaction with the drug target. Studies in vitro by Bilello et al. (1995, J. Infect. Dis. 171:546–551; 1996, Antimicrobiol. Agents Chemother. 40:1491–1497) have shown that the antiviral efficacy of two HIV PIs, A77003 and A80978, decreased as the concentration of AAG was increased and that the inhibition of HIV protease was highly correlated with the amount of intracellular inhibitor. Also, the clinical significance of these effects in vitro was shown by the lack of clinical efficacy of the HIV PI SC-52151, which has potent antiretroviral activity in vitro but inactivity in vivo, because extensive protein binding prevented intracellular diffusion (Fischl et al. J Acquir Immune Defic Syndr Hum Retrovirol 1997, 15:28–34). While there are extensive data to address this problem, no general correlation between protein binding and anti-HIV activity can be made so far on the basis of these studies.

Although the precise site of action of PIs has not been defined, the inhibition of HIV protease possibly takes place intracellularly. Bilello et al. (Bilello et al, 1996, Antimicrobiol. Agents Chemother. 40:1491–1497) have demonstrated that cellular uptake of protease inhibitor is proportionally decreased in the presence of AAG, which results in a decreased antiviral activity. These observations indicate that not only the antiviral $EC_{50}$ (50% effective concentration) of PIs, but also their interaction with human AAG, probably are the most important determinant factors of their anti-HIV efficacy in vivo because only free drug in plasma can equilibrate with intracellular compartments.

In determining therapeutic amounts and subsequent dosage regimens for individual protease inhibitors, it is clinically relevant to establish the binding affinities of the different protease inhibitors to plasma proteins. Also of interest is knowledge about plasma protein binding sites and the free drug concentrations. These factors and the information extracted therefrom can aid in obtaining a more complete pharmacokinetic profiling of protease inhibitors, which can result in more accurate and effective therapeutic amounts and dosage regimens for the protease inhibitors, which can ultimately translate into an improved treatment for HIV infected patients.

To date, binding of a particular protease inhibitor to plasma proteins is expressed as a percentage of total amount of drug that is bound to the plasma proteins (Sadler, et al. Antimicrob Agents Chemother. 2001 March;45(3):852–6; Anderson, et al, AIDS. 2000 Oct. 20;14(15):2293–7; Bilello, et al., J Infect Dis. 1995 March;171(3):546–51). This is number for a particular concentration of drug and plasma protein. It is well established that the concentration of plasma proteins, in particular the two most important ones in HIV/AIDS therapy AAG and serum albumin (HSA), is variable depending on age, race, and disease state (Kremer, et al. Pharmacol Rev. 1988 March;40(1):1–47). Furthermore, total drug concentration is also different in individuals due to the their various rate of absorption, distribution, metabolism, and excretion. Therefore, the use of percentage of bound and free forms is not useful and cannot be generally applied. However, if the dissociation constant, $K_d$, is directly determined for the binding of drug to the plasma protein, and the total drug and plasma concentration is known from pharmacokinetic studies, the concentrations of the free and bound form of drug can be readily calculated (Wyman, J. and Gill, S., "Binding and Linkage", 1990, Published by University Science Books, Mill Valley, Calif.).

Although considerable literature regarding the effect of AAG-binding on antiviral PIs has arisen (Billello et al. 1995, J. Infect. Dis. 171:546–551; Bilello et al. 1996, Antimicrobiol. Agents Chemother. 40:1491–1497; Lazdins et al. 1996, J. Infect. Dis. 175:1063–1070; Kiriyama et al. 1996, Biopharmac. Drug Dispos. 17:739–751; Zhang et al. 1999, J. Infect. Dis. 180:1833–1837; Jones et al. 2001, Br J Clin Pharmacol. 51:99–102; Kageyama et al. 1994, Antimicrob Agents Chemother. 22:499–506; Livingstone et al. 1995, J. Infect Dis. 172:1238–45), most methods for addressing this problem mainly use equilibrium dialysis, ultracentrifugation and ultrafiltration. To our knowledge, the binding affinities of PIs with AAG have not been determined using calorimetric methods. Moreover, the measurement of the thermodynamic parameters of a binding process provide a more realistic model.

In view of the clinical significance and the medical need to pharmacokinetically characterize protease inhibitors, a convenient and reliable method to measure the equilibrium dissociation constant, or a functional equivalent thereof, for the binding of a particular drug and plasma protein was designed. With the knowledge of the equilibrium dissociation constant, the in vivo activity of a particular PI in the presence of plasma proteins can be estimated using the EC50s from in vitro assays without plasma proteins. This will allow as well for an improved preclinical evaluation and selection of new PIs for future clinical development. Thus, the present invention concerns a method for determining the binding affinity of protease inhibitors to plasma proteins that is direct, has high sensitivity, and is easy to perform using routine laboratory procedures.

The present invention provides a method that can quantitatively calculate free drug concentrations of protease inhibitors in human plasma, as well as a method to calculate therapeutic amounts and dosage regimens.

Furthermore, the present invention provides a method that can calculate the effect of plasma proteins on the antiviral activity (EC50 values) of protease inhibitors from their binding affinities to plasma proteins. The present invention provides as well a method that can evaluate the in vivo anti-HIV efficacy of PIs in human plasma.

Often there may be competition between drugs in plasma protein binding, in which agents that are bound tightly, such as coumarin anticoagulants, macrolide or lincosamide antibiotics that bind tightly to alpha-1-acid Glycoprotein (AAG), are able to displace less tightly bound compounds from their binding sites and thus can increase the free form of the drug and improve the biological efficacy (Sommadossi, et al., 1998 U.S. Pat. No. 5,750,493). Therefore, the present invention provides as well a method for selecting compounds that competitively bind with plasma proteins, said selection being useful for co-administering agents to compete for plasma protein binding, so that an increase of the free plasma concentration of protease inhibitors can be achieved.

Figure 1:
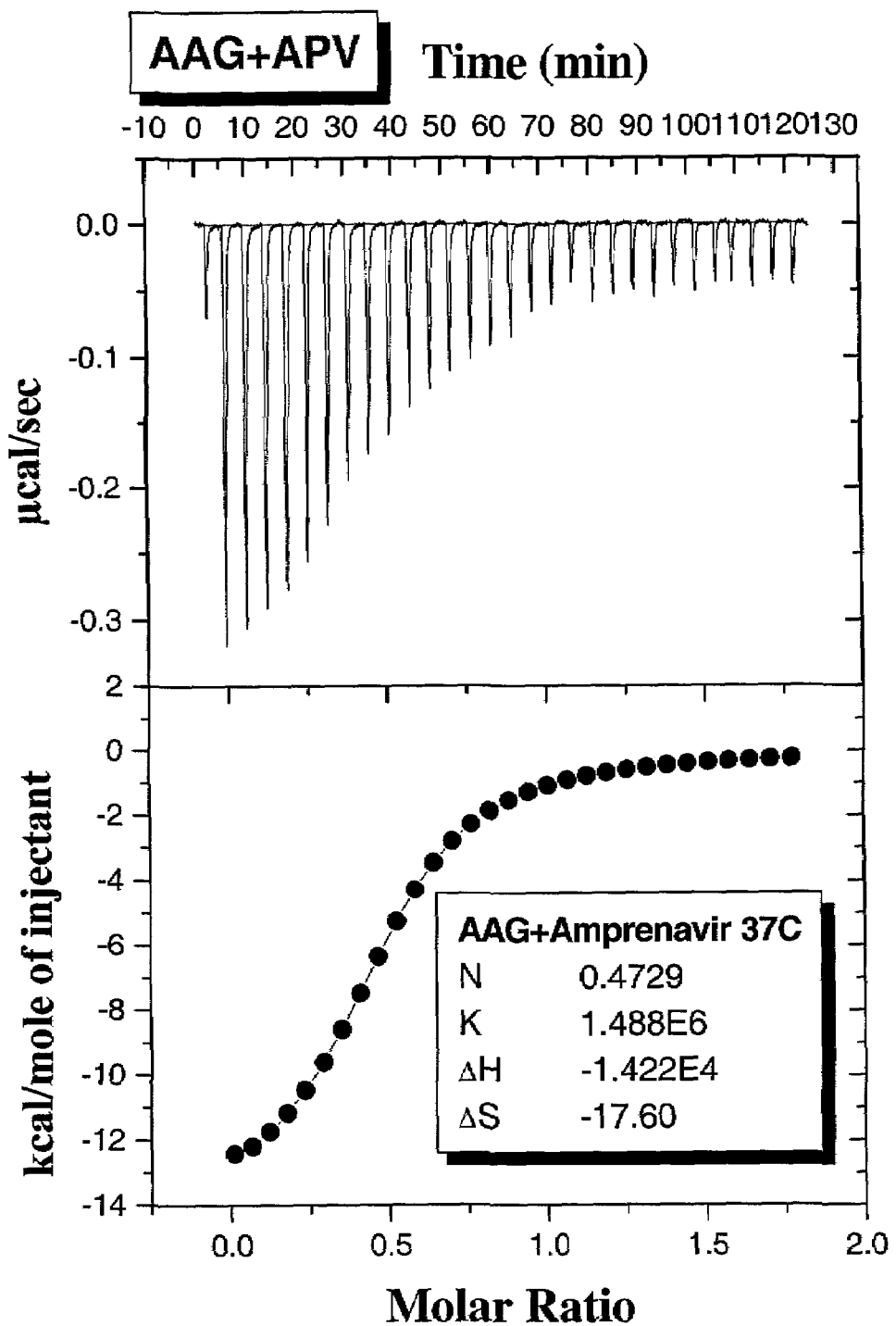
FIG. 1 shows Isothermal Titration Calorimetry measurements for the binding of Amprenavir to AAG.

Table 1 lists thermodynamic parameters of various PIs binding to AAG at 37° C. in 20 mM phosphate buffer, pH 7.4.

Table 2 lists binding affinities of 3 different PIs to AAG, their free drug concentrations, calculated IC50s, calculated efficacy, and IC50s values obtained from antiviral assays in the absence of AAG.

DETAILED DESCRIPTION

At all drug concentrations, the amount of a protein-bound drug depends on the affinity constant and the protein concentration and the present invention concerns a method to calculate the concentration of free drug available to block viral replication from the protein-drug affinity constants under physiologic circumstances. High sensitivity isothermal titration calorimetry (ITC) has been used in the present method to directly measure the binding thermodynamics, such as binding affinities ($K_a$), enthalpies ($\Delta H^0$), entropies ($\Delta S^0$) and binding free energies ($\Delta G^0$), of various PIs to AAG. Combined with the antiviral $EC_{50}$ values, the present method allows estimation of the antiviral $EC_{50}$ values in the presence of AAG and the in vivo efficacy of PIs.

Thus, the present invention provides a method for determining the binding affinity of at least one HIV protease inhibitor to at least one plasma protein comprising: i) providing at least one plasma protein; ii) providing at least one protease inhibitor; and iii) quantifying the binding affinity between the at least one plasma protein and the at least one protease inhibitor based on isothermal titration calorimetry measurement.

The term "binding" refers to an interaction or association between a minimum of two entities, or molecular structures, such as a ligand and an antiligand. The interaction may occur when the two molecular structures are in direct or indirect physical contact or when the two structures are physically separated but electromagnetically coupled there between, e.g. by hydrogen bonds or Van der Waals interactions. Examples of binding events of interest in a medical context include, but are not limited to, ligand/receptor, antigen/antibody, enzyme/substrate, enzyme/inhibitor, protein/protein, DNA/DNA, DNA/RNA, RNA/RNA, nucleic acid mismatches, complementary nucleic acids, nucleic acid/proteins, and plasma proteins/drugs.

The binding affinity of two molecules would therefore be the degree of interaction between two molecules. The binding affinity of plasma protein and a protease inhibitor can be expressed using various parameters such as the heat capacity change evolved on association of a protease inhibitor with a plasma protein ($\Delta C_p$); the equilibrium association binding constant ($K_a$) or the equilibrium dissociation constant ($K_d$), the free energy ($\Delta G$), the entropy of binding ($\Delta S$), or the enthalpy ($\Delta H$).

The data analysis of ITC results can be performed as described (Freire, et al., 1990, Anal. Chem., Vol 62: 950A–959A). Briefly, the isothermal titration calorimetry (ITC) measurements are designed to obtain primarily the enthalpy of each complex formation and their stoichiometries. The heats of each reaction are determined by integration of the peaks observed. After the contribution from the heat of dilution of each injection is subtracted, the heat is plotted against the molar ratio of PIs to AAG. The binding constant ($K_a$), enthalpy of binding ($\Delta H^0$), and stoichiometry (N) of the formation of complex are determined by fitting the binding isotherm against the binding equation using an independent binding model. Data analysis may be carried out with, for example, MicroCal ORIGN software, usually provided with the instrument.

HIV protease inhibitors include those compounds whose mechanism of action comprises an inhibition of the viral protease enzyme. As example, and with no limitation to future new compounds, HIV protease inhibitors include ritonavir (RTV), indinavir (IDV), nelfinavir (NFV), amprenavir (APV), telinavir (SC-52151), tipranavir (TPV), saquinavir (SQV), lopinavir (LPV), atazanavir, palinavir, mozenavir, BMS 186316, DPC 681, DPC 684, AG1776, GS3333, KNI-413, KNI-272, L754394, L756425, LG-71350, PD161374, PD173606, PD177298, PD178390, PD178392, PNU 140135, maslinic acid, U-140690, their prodrugs, metabolites, N-oxides and salts.

Plasma proteins include all proteins found endogenously in plasma. Examples of plasma proteins include without limitation Albumin (HSA), Alpha-1-acid Glycoprotein (AAG), Alpha-1-Antichymotrypsin, Alpha-1 Antitrypsin AT, alpha-fetoprotein, Alpha-1-microglobulin A1M, Alpha-2-Macroglobulin A2M, Angiostatin, Beta-2-Glycoprotein 1, Beta-2-microglobulin, Beta-2-Microglobulin B2M, Beta-N-Acetylglucosaminidase B-NAG, recombinant Centromere Protein B, Collagens (type 1-VI), Complement C1q, Complement C3, Complement C4, Ceruplasmin, Chorionic Gonadotrophin HCG, Chorionic Gonadotrophin Beta CORE BchCG, C-Reactive Protein CRP, CK-MB (Creatine Kinase-MB), CK-MM & CK-BB, Cystatin C, D-Dimer, dsDNA, Ferritins, Glycogen Phosphorylase ISO BB, Haptoglobulin, IgA, IgE, IgG, IgG, IgM, Kappa light chain, lambda light chain, recombinant LKM Antigen, La/SS-B, Lysozyme, Myelin Basic Protein, Myoglobin, Neuron-Specific Enolase, Placental Lactogen, Prealbumin, Pregnancy assoc Plasma Protein A, Pregnancy specific beta 1 glycoprotein (SP1), Prostate Specific Antigen PSA, PSA-A1-Act complex, Prostatic Acid Phosphatase PAP, Proteinase 3 (PR3/Anca), Prothrombin, Retinol Binding Globulin RBP, recombinant human RO/SS-A 52 kda, recombinant human RO SS-A 60 kda, Sex Hormone Binding Globulin SHBG, S100 (BB/AB), S100 BB homodimer, Thyroglobulin Tg, Thyroid Microsomal Antigen, recombinant thyroid peroxidase TPO, Thyroid Peroxidase TPO, Thyroxine Binding Globulin TBG, Transferrin, Transferrin receptor, Troponin I complex, Troponin C, Troponin I, Troponin T, and Urine Protein 1. Plasma proteins most associated with protease inhibitors include albumin, $\alpha_1$-acid glycoprotein and lipoproteins.

Plasma proteins may also encompass proteins of external origin, which are not necessarily forming part of the physiological population, but may be found in the body, i.e. proteins from diet origin or from drug compositions.

Particular plasma proteins may have several variants. The term "protein variant" refers to a polypeptide comprising one or more substitutions of the specified amino acid residues underlying the protein. The total number of such substitutions is typically not more than 10, e.g. one, two, three, four, five or six of said substitutions. In addition, the protein variant may optionally include other modifications of the parent enzyme, typically not more than 10, e.g. not more than 5 such modifications. The variant generally has a homology with the parent enzyme of at least 80%, e.g. at least 85%, typically at least 90% or at least 95%. Variants may not only differ in primary structure (amino acid sequence), but also in secondary or tertiary structure and the amount and structure of covalently attached carbohydrates. A protein may be present in plasma in different variants, at similar or different concentrations. Variants of a protein may exhibit different binding properties. For instance human $\alpha$-1 acid glycoprotein is present in two different variants, A and F1/S, which have different binding properties to various ligands and drugs.

The methods of the present invention may additionally comprise as part of the test composition, any compound, including, but not limited to, dipeptides, tripeptides, polypeptides, proteins, small and large organic molecules, buffers, or test aid components, and derivatives thereof. In a particular embodiment, the method preferably includes a competitive binding agent. A competitive binding agent refers to those molecules that competitively bind to plasma proteins in the presence of protease inhibitors. Said competitive binding agent could be one or two more drugs, for example other drugs than antivirals which bind to plasma proteins, also for example one or two more drugs effective to treat AIDS and related syndromes, also for example one or two more antivirals, such as NNRTI, NRTI, PI, fusion inhibitors, entry inhibitors, integrase inhibitors, so concomitant administration of antiretrovirals, optionally with other types of drugs, and its influence on plasma protein binding properties may be studied. Therefore, the present invention also provides a method for selecting compounds that bind competitively to plasma proteins in the presence of protease inhibitors. Said compounds may be used as co-administered agents to increase the free plasma concentration of protease inhibitors.

In another embodiment, the different methods of the present invention may comprise physiological fluid, or have the same components thereof, for example the physiological fluid is blood, for example plasma, also for example serum.

In another embodiment of the present invention, there is provided a method for determining the concentration of at least one protease inhibitor present in free form within a test medium, said test medium also containing a bound form of said protease inhibitor with at least one plasma protein, in equilibrium with said free form, the method comprising the steps of: i) providing at least one plasma protein, ii) providing at least one protease inhibitor; iii) quantifying the concentration of protease inhibitor in free form based on isothermal titration calorimetry measurements.

The quantification of the concentration of protease inhibitor in free form maybe performed by direct measurement of binding affinity $K_d$ using isothermal titration calorimetry; and calculating the concentration of protease inhibitor in free form using the formula:

$$[drug]_{free} = \frac{1}{2}\left[\sqrt{(P_t - L_t + K_d)^2 + 4K_d L_t} - (P_t - L_t + K_d)\right] \quad \text{Equation 1}$$

where $P_t$ and $L_t$ are total protein and drug concentrations, and $K_d$ is the equilibrium dissociation constant obtained in step (iii).

Optionally, the formula to be applied may be:

$$PL = \frac{(K_a L_0 + nK_a P_0 + 1) - \sqrt{(K_a L_0 + nK_a P_0 + 1)^2 - 4nK_a^2 P_0 L_0}}{2nK_a} \quad \text{Equation 2}$$

where PL is the protein-bound concentration of PIs, $L_0$ and $P_0$ are the total concentration of PIs and plasma protein, $K_\alpha$ and n are the binding constants and number of binding sites, respectively. The concentrations of free PIs may be then calculated by subtraction of the bound concentration from the total concentration, equation 3, $$L_{free} = L_0 - PL \quad \text{Equation 3}$$

Additionally, the method for calculating the free concentration of protease inhibitors available to inhibit viral replication may be performed by obtaining the $K_a$ (or association constant) from isothermal titration calorimetry measurement under different plasma protein concentrations, preferably physiological concentrations.

The concentration or amount of protease inhibitor present in free form is particularly useful to establish pharmacokinetic characteristics such as the distribution volume, half-life, bioavailability, and to further determine the therapeutic amount, dosage amounts and dosage intervals, necessary to accomplish an effective therapeutic treatment. Thus, the concentration or amount of protease inhibitor present in free form allows the design of a dosage regimen for a given drug. Same information may be used for patient management, therapeutic drug monitoring, thus, to adjust and tailor the dosage regimen for individual patients and conditions.

The present invention further provides a method of constructing a binding affinity and pharmacokinetic profile database of HIV protease inhibitors, with plasma proteins, and variants thereof, comprising: i) providing at least one plasma protein, and variants thereof; ii) providing at least one protease inhibitor; iii) quantifying the binding affinity between the at least one plasma protein and the at least one protease inhibitor based on isothermal titration calorimetry measurements; and/or quantifying the concentration of protease inhibitor in free form based on isothermal titration calorimetry measurements; iv) correlating in a data table the binding affinity or the concentration of protease inhibitor in free form, with the dosage regimens. Said method for constructing such database also encompasses reports that are generated comprising a listing, analysis, or other information regarding the binding affinities, pharmacokinetic parameters, and their correlation to drug dosage regimens identified by the methods of the invention.

In another embodiment of the present invention, there is provided a method for determining the antiviral activity or EC50 value of at least one HIV protease inhibitor in the presence of at least one plasma protein comprising: providing at least one plasma protein; providing at least one protease inhibitor; quantifying the binding affinity between the at least one plasma protein and the at least one protease inhibitor based on isothermal titration calorimetry measurements.

The quantification of the antiviral activity or EC50 value of a protease inhibitor in the presence of at least one plasma protein may be performed by direct measurement of binding affinity $K_a$ using isothermal titration calorimetry; and calculating the antiviral activity or EC50 value of the protease inhibitor using the formula:

$$EC50_{\text{in plasma protein}} = EC50 + \frac{K_a \cdot C_{plasma\,protein}}{K_a + \frac{1}{EC50}} \quad \text{Equation 4}$$

where, $EC_{50}$ is the 50% of effective concentration of at least one protease inhibitor in a cell-based assay without plasma proteins, and $C_{plasma\,protein}$ is the plasma protein concentration.

In another embodiment of the present invention there is provided a method for determining the in vivo efficacy of at least one HIV protease inhibitor in human plasma protein based on determining the concentration of at least one protease inhibitor present in free form as explained above.

The quantification of the in vivo efficacy of a protease inhibitor in human plasma may be performed by direct measurement of binding affinity $K_d$ using isothermal titration calorimetry; calculating the concentration of protease inhibitor in free form using the formulas described above; and calculating the in vivo efficacy of the protease inhibitor in human plasma using the formula:

$$\text{Efficacy} = \frac{C_{free}}{EC_{50}} \quad \text{Equation 5}$$

where, $C_{free}$ is the concentration of protease inhibitor in free form, the EC50 is the 50% of effective concentration of at least one protease inhibitor in a cell-based assay without plasma proteins.

Furthermore, the present invention provides a method of constructing a binding affinity and antiviral activity and/or efficacy database of HIV protease inhibitors, with plasma proteins, and variants thereof, comprising: i) providing at least one plasma protein, and variants thereof; ii) providing at least one protease inhibitor; iii) quantifying the binding affinity between the at least one plasma protein and the at least one protease inhibitor based on isothermal titration calorimetry measurements; and/or quantifying the concentration of protease inhibitor in free form based on isothermal titration calorimetry measurements; iv) correlating in a data table the binding affinity and/or the concentration of protease inhibitor in free form, with the antiviral activity and/or efficacy. Said method for constructing such database also encompasses reports that are generated comprising a listing, analysis, or other information regarding the binding affinities, free drug concentrations, pharmacodynamics' parameters, and their correlation to antiviral activities and efficacies determined by the methods of the invention.

Another embodiment of the invention is a kit comprising i) at least one plasma protein, and ii) at least one protease inhibitor. Said kit may be directed to determining the binding affinity of at least one HIV protease inhibitor to at least one plasma protein. Additionally, the kit may be used for determining the concentration of at least one protease inhibitor present in free form within a test medium, said test medium also containing a bound form of said protease inhibitor with at least one plasma protein in equilibrium with said free form.

In another embodiment of the invention there is a kit comprising at least one plasma protein, and at least one protease inhibitor; and directed to determining the EC50 value of at least one HIV protease inhibitor to at least one plasma protein. Optionally, the same kit may be used for determining the in vivo efficacy of at least one HIV protease inhibitor in human plasma.

The kits may further comprise any reagents necessary to practice the methods of the invention and any equipment or apparatus needed to practice the methods of the invention, such as the equipment necessary to measure binding affinity.

The methods provided in the present invention may optionally be used as or comprise part of a high-throughput screening assay where numerous test compositions are evaluated for their effect on binding affinity of the at least one plasma protein and the at least one protease inhibitor and for the pharmacokinetic derived properties of the protease inhibitors.

The order of the steps of the methods of the invention may be varied. One of skill in the art would be able to determine which variations in the order of the steps are applicable.

Other embodiments of the invention will be apparent to those skilled in the art from consideration of the specification and practice of the invention disclosed herein. It is intended that the specification and examples be considered as exemplary only, with a true scope and spirit of the invention being indicated by the claims.

EXAMPLE 1

Thermodynamic Equilibrium Binding Assay Using ITC

Binding experiments were run using Isothermal Titration Calorimetry (ITC) to measure bound and unbound protease inhibitors.

Sample preparation: Solutions of AAG and its variants for ITC experiments were made up in 20 mM sodium borate buffer, pH 7.4. All compounds were prepared as stock solution of 20 mM or 25 mM in DMSO and thereafter diluted to desired concentration in the same buffer. For all ITC experiments, the percentage of DMSO is below 1%.

ITC Experiments: The isothermal titration measurements of the binding of various PIs to AAG can be typically carried out at 37° C. using a VP-ITC titration calorimeter (MicroCal, Northampton, Mass.). The instrument was electrically calibrated by means of a standard electric pulse as recommended by the manufacturer. For the PIs binding to AAG, solutions of PI (80~100 µM) were used to titrate AAG (10~12 µM). A 300 µL syringe was used for the titrant, mixing was effected by stirring this syringe at 300 rpm during equilibration and experiment. Typically after a preliminary 2 µL injection, 25 injections of 10 µL each were performed with a 250s interval between injections in a single titration. The reference cell of the calorimeter filled with water, acts as a thermal reference to the sample cell. To correct for PIs heats of dilution, the control experiments were also performed using similar conditions with buffer solution only. All solutions were degassed before titrations to reduce the noise. The buffer contained 20 mM sodium phosphate, pH 7.4.

Figure 2:
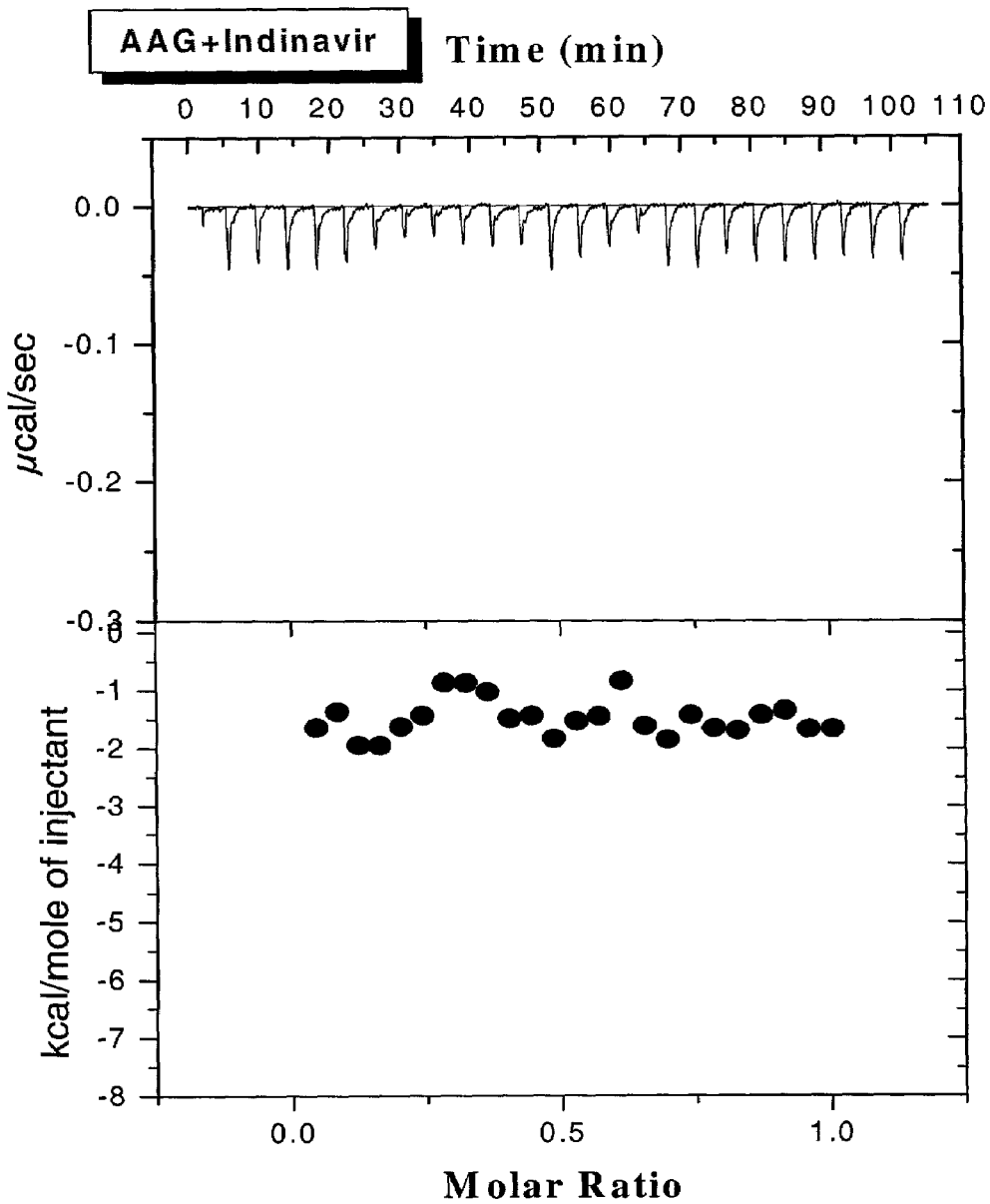
FIG. 2 shows Isothermal Titration Calorimetry measurements for the binding of Indinavir to AAG.

Two typical titration calorimetry measurements under same condition are shown in FIGS. 1 and 2. The upper panels in FIGS. 1 and 2 show the traces recorded for each 10 µL injection of 80 µM APV and IDV into 12 µM, 1.45 mL of AAG, respectively. The titration profiles for APV and IDV clearly indicate that APV binds to AAG accompanied with an exothermic heat effect, whereas IDV does not bind to AAG under the conditions studied. The area of each peak was integrated and corrected for the PI heat of dilution, which was estimated by a separate experiment by injecting the PI into the buffer. By fitting the titration curve with a nonlinear least-squares method, the enthalpy change $\Delta H^0$, and the binding constant $K_a$ of PI binding to AAG can be estimated with the assumption of an independent binding site model. Lower panels of FIGS. 1 and 2 show the best least-squares fit of each integrated heat. The results obtained by this curve fitting using the calorimetric software supplied with the calorimeter for the APV binding to AAG are $K^a=1.49(\pm0.20)\times10^6 M^{-1}$ and $\Delta H^0=-14.2\pm0.5$ kcal·mol$^{-1}$.

The complete thermodynamics of various PIs binding to AAG at 37° C. in 20 mM phosphate buffer, pH 7.4 are summarized in Table 1. The values provided are the average of duplicate experiments. For all the PIs studied binding to AAG, we obtained exothermic enthalpy. The standard free energies ($\Delta G^0$) were obtained from the equation $\Delta G^0 = -RT \ln K_a$, in which the $K_a$ is the binding constant at 37° C. The $\Delta S^0$ function was calculated from the standard thermodynamic relation $\Delta G^0 = \Delta H^0 - T\Delta S^0$. The fold increase EC50 is the change in experimental EC50s obtained from cell-based assays in the absence of AAG and in the presence of 1 mg/mL AAG, according to the method described by Pauwels et al., Rapid and automated tetrazolium-based calorimetric assay for the detection of anti-HIV compounds, J. Virol. Methods, 1988, 20(4), 309–21.

TABLE 1

| PIs | Fold Inc. EC$_{50}$ | $K_a$ ($10^6 M^{-1}$) | $\Delta H$ (kcal/mol) |
|---|---|---|---|
| IDV | 1.0 | No binding | / |
| RTV | 18.9 | 1.55 ± 0.49 | −2.58 ± 0.16 |
| NFV | 22.9 | 2.35 ± 0.42 | −4.26 ± 0.09 |
| APV | 23.7 | 1.49 ± 0.20 | −14.22 ± 0.49 |
| SC-52151 | 29.2 | 2.38 ± 0.60 | −1.33 ± 0.05 |
| SQV | 5.6 | 0.34 ± 0.12 | −3.57 ± 0.21 |
| LPV | 37.1 | 5.77 ± 0.72 | −5.68 ± 0.07 |
| KN1764 | N/A | 1.24 ± 0.27 | −7.65 ± 0.40 |

EXAMPLE 2

Figure 3:
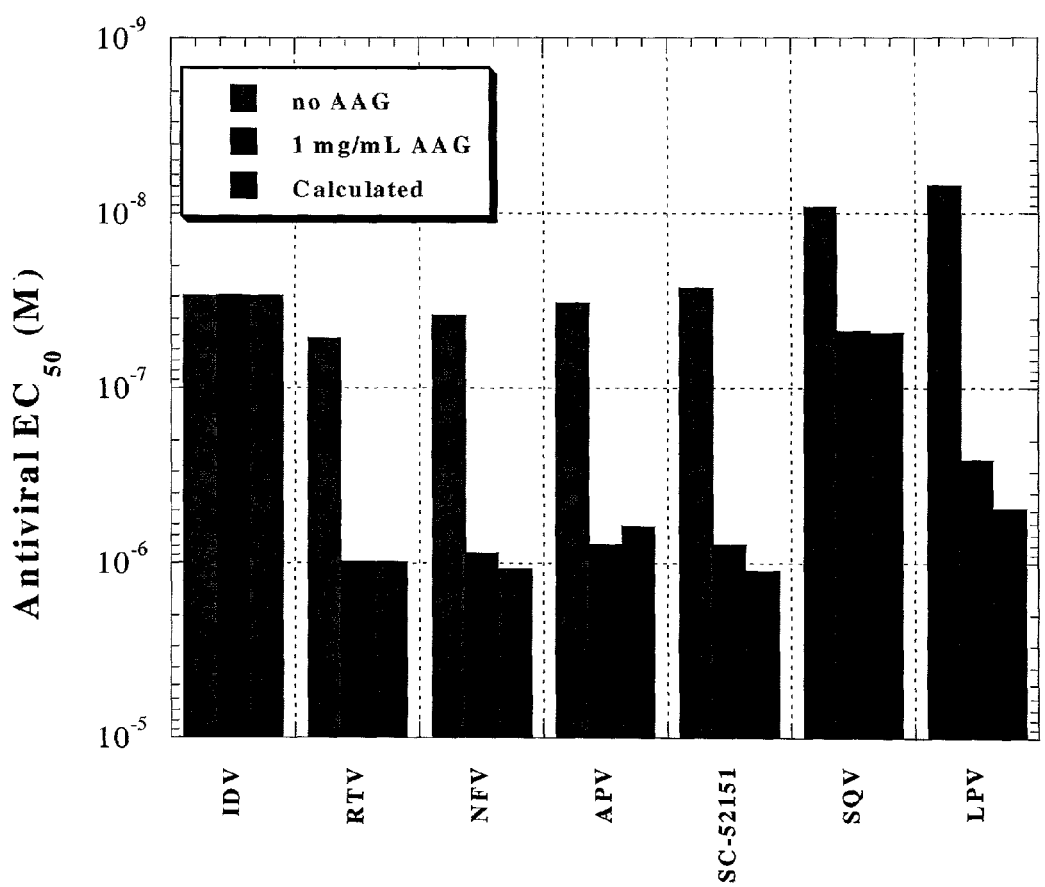
FIG. 3 shows a comparison for various PIs of the calculated EC50, and the experimental EC50 in the presence of 1 mg/mL AAG and in the absence of AAG.
Figure 4:
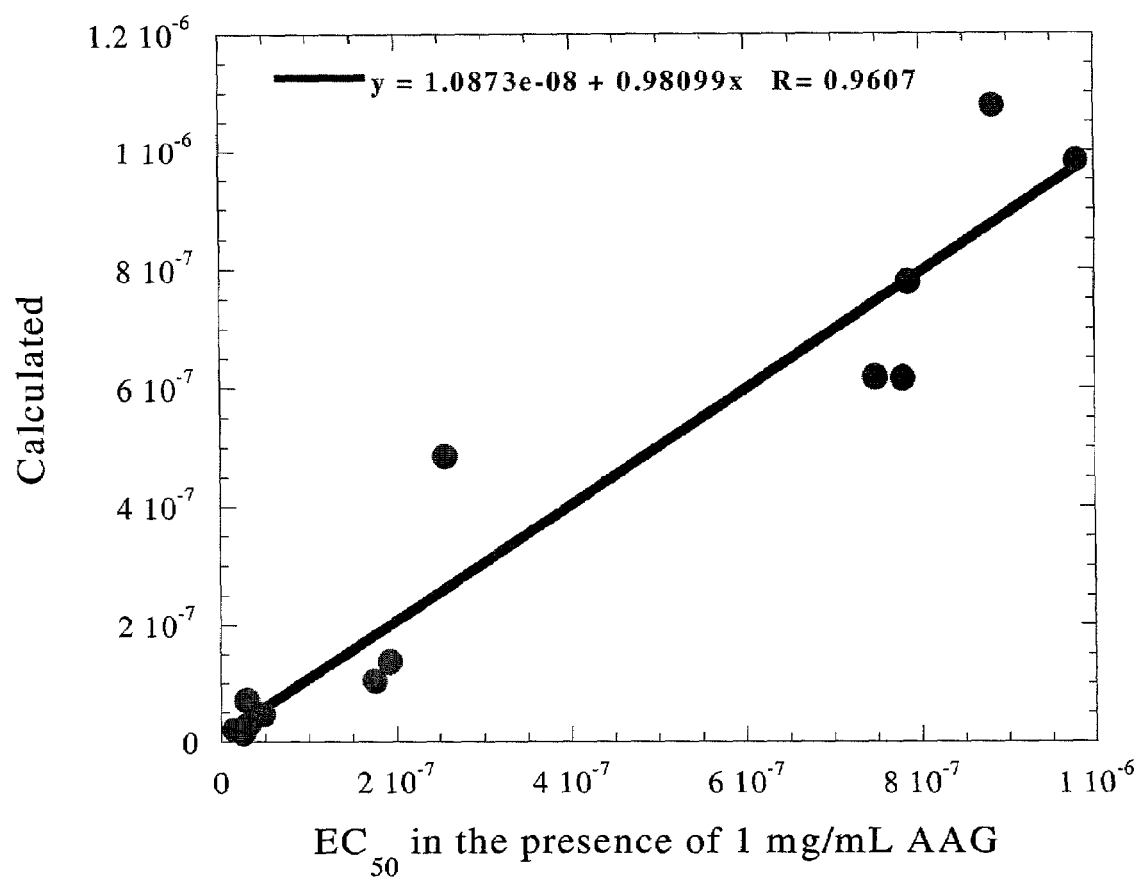
FIG. 4 shows a correlation analysis of calculated EC50 versus experimental EC50 for various PIs.

Ka can be Utilized to Predict the Effect of AAG on EC50 Value in Cell-based Antiviral Assays In order to determine whether there is a strong correlation between the loss of activity of PIs in presence of AAG and their binding affinities measured directly by ITC, the antiviral EC$_{50}$ of these PIs in the presence of 1 mg/mL of AAG from their binding constants $K_a$ with AAG and their EC$_{50}$ in the absence of AAG was calculated according to Equation 4. FIG. 3 shows the calculated and experimental EC$_{50}$ of 7 PIs studied here in the presence of 1 mg/mL AAG and in the absence of AAG. As discussed above, the addition of 1 mg/mL AAG in the cell culture markedly decreased the EC$_{50}$ of PIs except IDV, herein we consider the presence of AAG has no effect on $EC_{50}$ of IDV. Comparison of the calculated and experimental $EC_{50}$ of these PIs in the presence of AAG revealed that the calculated and experimental values were highly consistent (FIG. 3). FIG. 4 shows the calculated $EC_{50}$ versus experimental $EC_{50}$, the correlation analysis between these values yields a slope of 0.982 with a correlation coefficient of 0.96. This excellent correlation strongly convinced the validation of the present calculation method. It was demonstrated that the inhibitory effect of AAG on the in vitro activity ($EC_{50}$) of PIs is highly correlated with their binding affinities with AAG.

EXAMPLE 3

Figure 5:
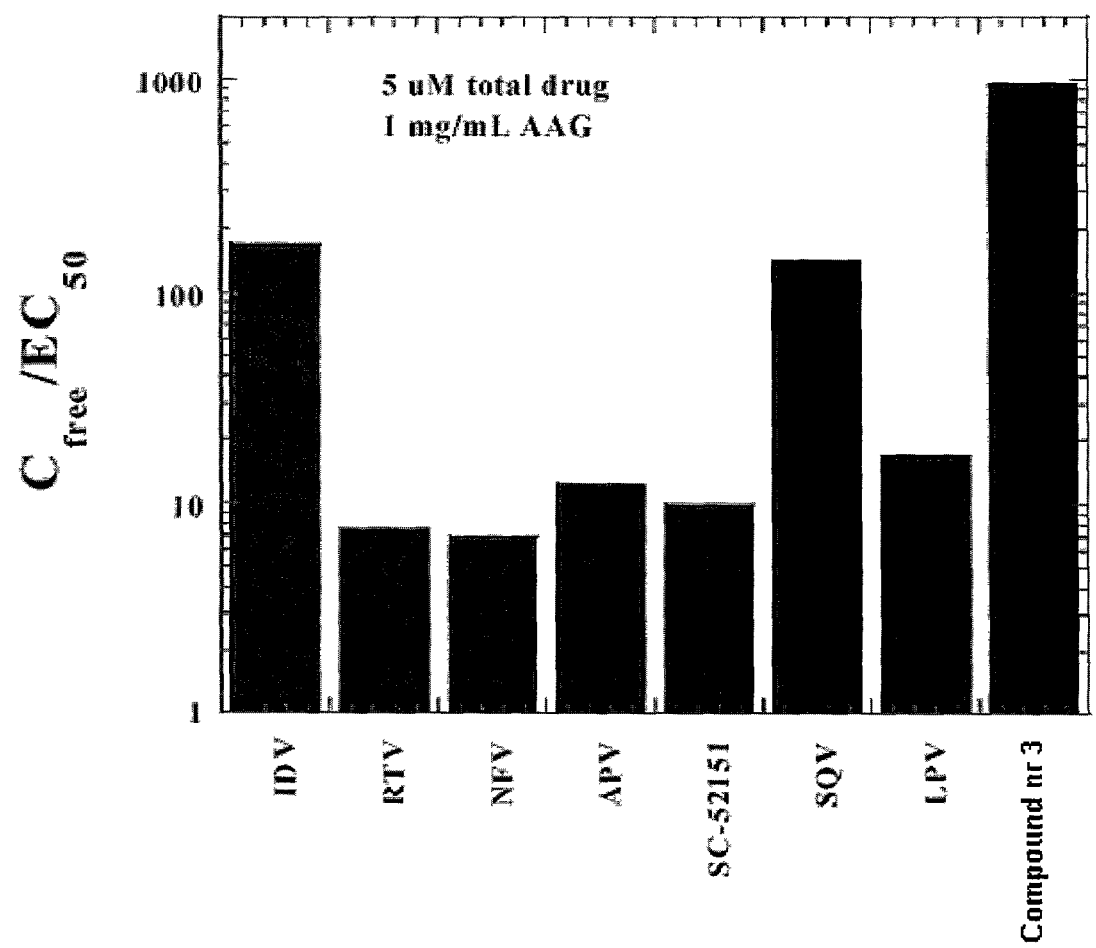
FIG. 5 shows the in vivo efficacies of various PIs calculated from their free drug concentrations.

Comparative Evaluation of the in vivo Antiviral Efficacy of PIs in the Presence of AAG The evaluation of the relative in vivo efficacy of PIs in human plasma from their $EC_{50}$ (Equation 5) is shown in FIG. 5. The validation of the correct equation was confirmed using published data for three PIs monotherapy trials.

EXAMPLE 4

Data Table

In table below, a data table with the binding affinity of 3 PI's to AAG (Ka), their free drug concentrations, calculated IC50s, and calculated efficacy were extracted from the ITC results and compared to IC50s from an antiviral assay in the absence of AAG. The predicted and experimental IC50s showed a good correlation.

TABLE 2

| ID | IC50 | Ka to AAG | Predicted IC50 @ 1 mg/mL AAG | Free drug Concentration (M) | "Efficacy" |
|---|---|---|---|---|---|
| 1 | 3.00E−09 | 1.92E+06 | 7.46E−08 | 1.30E−06 | 432.16 |
| 2 | 8.00E−10 | 2.19E+06 | 2.27E−08 | 1.19E−06 | 1484.7 |
| 3 | 5.00E−10 | 1.24E+06 | 8.25E−09 | 1.71E−06 | 3419.8 |

Compound number 1

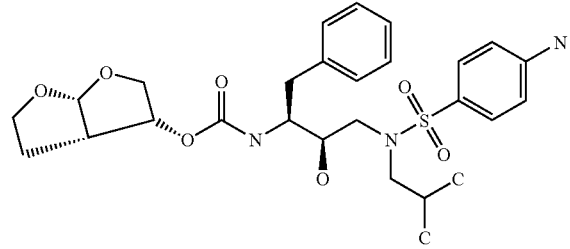

TABLE 2-continued

| ID | IC50 | Ka to AAG | Predicted IC50 @ 1 mg/mL AAG | Free drug Concentration (M) | "Efficacy" |
|---|---|---|---|---|---|

Compound number 2

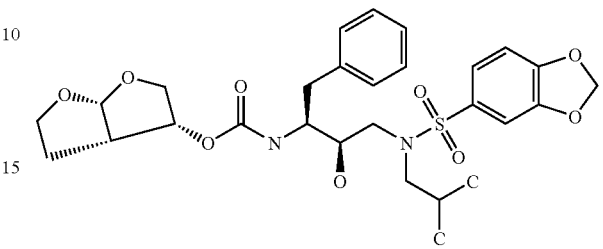

Compound number 3

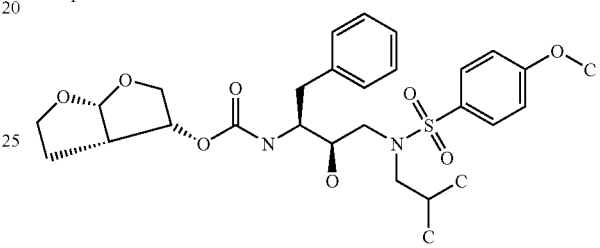

We claim:

1. A method for determining the binding affinity of at least one protease inhibitor to at least one plasma protein comprising:
   i) providing at least one plasma protein;
   ii) providing at least one protease inhibitor;
   iii) quantifying the binging affinity between the at least one plasma protein and the at least one protease inhibitor through isothermal titration calorimetry measurements.

2. A method according to claim 1, wherein the plasma protein is chosen from albumin, α1-acid glycoprotein, and lipoprotein.

3. A method according to claim 1, wherein said method is a high throughput screening method.

* * * * *

UNITED STATES PATENT AND TRADEMARK OFFICE
CERTIFICATE OF CORRECTION

| | | |
|---|---|---|
| PATENT NO. | : 7,087,373 B2 | Page 1 of 1 |
| APPLICATION NO. | : 10/161613 | |
| DATED | : August 8, 2006 | |
| INVENTOR(S) | : Doug Xie et al. | |

It is certified that error appears in the above-identified patent and that said Letters Patent is hereby corrected as shown below:

<u>Column 12,</u>

Line 41, delete "binging" and insert -- binding --.

Signed and Sealed this

Ninth Day of January, 2007

JON W. DUDAS
*Director of the United States Patent and Trademark Office*